United States Patent
Giordan et al.

(10) Patent No.: US 10,064,887 B2
(45) Date of Patent: Sep. 4, 2018

(54) PHARMACEUTICAL COMPOSITIONS CONTAINING HYALURONIC ACID FOR USE IN THE TREATMENT OF BLACK DISC DISEASE

(71) Applicant: FIDIA FARMACEUTICI S.P.A., Abano Terme (PD) (IT)

(72) Inventors: Nicola Giordan, Abano Terme (IT); Pierangelo Bellato, Abano Terme (IT)

(73) Assignee: FIDIA FARMACEUTICI S.P.A., Abano Terme (PD) (IT)

( * ) Notice: Subject to any disclaimer, the term of this patent is extended or adjusted under 35 U.S.C. 154(b) by 0 days.

(21) Appl. No.: 14/786,126

(22) PCT Filed: Apr. 23, 2014

(86) PCT No.: PCT/IB2014/060928
§ 371 (c)(1),
(2) Date: Oct. 21, 2015

(87) PCT Pub. No.: WO2014/174450
PCT Pub. Date: Oct. 30, 2014

(65) Prior Publication Data
US 2016/0067274 A1    Mar. 10, 2016

(30) Foreign Application Priority Data

Apr. 24, 2013   (IT) .............................. PD2013A0110

(51) Int. Cl.
| | | |
|---|---|---|
| *A61K 31/728* | (2006.01) | |
| *A61L 27/20* | (2006.01) | |
| *A61L 27/52* | (2006.01) | |
| *A61K 9/06* | (2006.01) | |
| *A61K 45/06* | (2006.01) | |
| *A61L 27/54* | (2006.01) | |

(52) U.S. Cl.
CPC .............. *A61K 31/728* (2013.01); *A61K 9/06* (2013.01); *A61K 45/06* (2013.01); *A61L 27/20* (2013.01); *A61L 27/52* (2013.01); *A61L 27/54* (2013.01); *A61L 2300/402* (2013.01); *A61L 2300/41* (2013.01); *A61L 2300/432* (2013.01); *A61L 2430/38* (2013.01)

(58) Field of Classification Search
None
See application file for complete search history.

(56) References Cited

U.S. PATENT DOCUMENTS

| | | | |
|---|---|---|---|
| 2008/0075657 A1 | 3/2008 | Abrahams et al. | |
| 2008/0103564 A1* | 5/2008 | Burkinshaw ..... | A61B 17/00491 607/96 |

FOREIGN PATENT DOCUMENTS

WO    WO 2011/000820 A2    1/2011

OTHER PUBLICATIONS

Gloria, A., Borzacchiello, A., Causa, F., & Ambrosio, L. (2012). Rheological characterization of hyaluronic acid derivatives as injectable materials toward nucleus pulposus regeneration. Journal of biomaterials applications, 26(6), 745-759.*
Revell, P. A., Damien, E., Di Silvio, L., Gurav, N., Longinotti, C., & Ambrosio, L. (2007). Tissue engineered intervertebral disc repair in the pig using injectable polymers. Journal of Materials Science: Materials in Medicine, 18(2), 303-308.*
Finelli, I., Chiessi, E., Galesso, D., Renier, D., & Paradossi, G. (2011). A new viscosupplement based on partially hydrophobic hyaluronic acid: a comparative study. Biorheology, 48(5-6), 263-275.*
International Search Report, issued in PCT/IB2014/060928, dated Sep. 24, 2014.
Written Opinion of the International Searching Authority, issued in PCT/IB2014/060928, dated Sep. 24, 2014.

* cited by examiner

*Primary Examiner* — Shaojia A Jiang
*Assistant Examiner* — Dale R Miller
(74) *Attorney, Agent, or Firm* — Birch, Stewart, Kolasch & Birch, LLP

(57) ABSTRACT

The present invention describes and claims pharmaceutical compositions in gel form for use in the treatment of intervertebral disc degeneration, in particular the forms of dehydration and emptying of the nucleus pulposus known as "black disc disease". These compositions comprise a hyaluronic acid derivative which forms hydrogels with precise rheological characteristics that make it ideal for filling the nucleus pulposus.

5 Claims, No Drawings

PHARMACEUTICAL COMPOSITIONS CONTAINING HYALURONIC ACID FOR USE IN THE TREATMENT OF BLACK DISC DISEASE

FIELD OF INVENTION

The present invention relates to pharmaceutical compositions in the form of hydrogels for use in the treatment of intervertebral disc degeneration, in particular the forms of dehydration and emptying of the nucleus pulposus known as "black disc disease".

TECHNICAL BACKGROUND

The generic term "back pain" comprises a wide range of disorders, whose definition is often uncertain and whose etiology is difficult to classify, characterised by a common symptom: "backache". The lumbosacral section of the spinal column is a crucial structure; of all the transitional hinges, it is certainly the one that comes under most stress, but is also the most mobile, which exposes it to continual overloads and imbalances. The focal point of the spinal column is the intervertebral disc. It is contained between all types of vertebrae, and comprises two concentric sub-structures: the external annulus fibrosus, which surrounds the internal nucleus pulposus. The annulus fibrosus is a stratified elastic tissue consisting of extracellular matrix enriched with a series of protein fibres (mainly type II collagen) arranged in a zigzag pattern, i.e. not vertically oriented. Specifically, the ring consists externally of type I collagen fibres (known as Sharpey's fibres), while the central part consists of type II collagen and chondrocytes. The nucleus pulposus is a gelatinous tissue mainly consisting of water (about 85% in volume in healthy young people), imbibed by a proteoglycan matrix (mostly consisting of hyaluronate, chondroitin and keratan sulphate) produced by the chondrocytes that reside in the innermost part of the annulus fibrosus. The nucleus pulposus acts as a bearing, which supports and distributes the compressive forces to which the spinal column is continually subjected; the annulus fibrosus supports the tensile forces and provides mechanical support and stability for the spine. The intervertebral disc is an avascular structure, which obtains its nourishment from the blood vessels that supply the adjacent bone structures.

As a result of microtraumas, or more simply advancing age, especially at lumbosacral level, the intervertebral disc undergoes structural modifications that give rise to the disorder known as "intervertebral disc degeneration" (Yong-Soo, *Asian Spine Journal*, 2009, 3, 39-44). It involves a set of complex phenomena, whose etiology is not always uniform, and which has different clinical characteristics. It ranges from asymptomatic degeneration, found in younger people, to particularly painful forms complicated by major postural alterations. The latter usually (but not always) occur in elderly people, and can be caused by trauma, wear and tear, malnutrition or simply, as stated, aging of the structures that make up the intervertebral disc. The various forms of intervertebral disc degeneration include one characterised by a reduction in water content, leading to a reduction in and modification of the structure of the proteins and proteoglycans that make up the nucleus pulposus; it becomes dehydrated, empties, and loses its gelatinous structure and the clear demarcation from the annulus fibrosus. The degenerative alteration of the disc is clearly shown on NMR scans; it appears globally thinner than healthy discs and shows a change of colour to various shades of black, due to the reduction in the water content of the nucleus pulposus. This pathological situation is known as black disc disease. The thinning, as well as reducing the ability of the disc to absorb shocks and provide stability for the spine, is nearly always accompanied by the release of inflammatory factors, which generate intense pain (Rengachary et al., *Neurosurg Focus*, 2002, 13, E14).

In the later stages of disc disease, the nucleus pulposus may also press on the annulus fibrosus ("bulging"), which may rupture, giving rise to a hernia.

In less serious cases, a conservative approach is taken, based on physiotherapy associated with pain control, as the pain is very acute and disabling. As the classic painkillers have little or no effect, treatment with ozone, administered by injection, has been successfully used for some time; this treatment exploits the powerful antioxidant, anti-inflammatory and therefore painkilling action of ozone.

In the most serious cases, in addition to pain control, strategies which are effective from the functional standpoint and are curative of black disc disease are sought, i.e. strategies which at least partly reduce the cause, and restore the structure and functionality of the nucleus pulposus. In the vast majority of cases black disc disease is accompanied by postural defects, which in turn generate further stiffness and pain.

One approach is to administer cells able to produce proteoglycan matrix, such as mesenchymal stem cells from bone marrow, possibly combined with molecules that promote the formation of matrix by the residual cells (such as growth factors) and with inflammatory cytokine inhibitors, into the nucleus pulposus. This approach attempts to restore the proteoglycan matrix and to control the pain.

However, these treatments are still experimental, and require thorough verification, because they are particularly problematic (as regards the number of cells to be used, the active substances and their concentrations and the type of carrier, for example). However, the usefulness of administering cells to the nucleus pulposus is somewhat controversial; as previously stated, this structure does not originally contain cells, and is avascular, which means that the proliferation of the cells introduced depends on the blood supply of the surrounding structures, which is sure to be impaired in pathological situations.

The technique that involves introducing into the nucleus pulposus a "bearing" able to absorb and distribute compressions, thus recreating a condition similar to the physiological condition, is much more promising.

The Applicant has found and demonstrated that a "bearing" consisting of a hydrogel with the following characteristics is particularly suitable for this type of application:
- it can be implanted by minimally invasive, preferably injectable techniques, and is therefore easily extrudable;
- it remains in situ without slipping away from the site of implantation because it has precise rheological characteristics;
- it possesses mechanical properties (elasticity, compressibility) suitable to support and redistribute compressions;
- it is highly hydratable;
- it is absolutely safe, both in its unmodified form and as degradation products, inevitably originating from physiological enzyme activity.

The hydrogel whose efficacy is demonstrated by the Applicant below consists of a hyaluronic acid derivative. Hyaluronic acid (HA) is a linear-chain heteropolysaccharide consisting of alternating residues of D-glucuronic acid and N-acetyl-D-glucosamine. It is present in nature in pericellular gels, in the ground substance of the connective tissue of vertebrates (of which it is one of the main constituents), in the synovial fluid of the joints, and in the vitreous humour and umbilical cord. HA therefore plays an important role in the biological organism, both as a mechanical support for the cells of many tissues, such as skin, tendons, muscles and cartilage, and as a viscous fluid that absorbs shocks and ensures that the joint surfaces can slide over one another.

Native hyaluronic acid has an extremely variable average molecular weight (MW), depending on the source from which it is obtained and the preparation methods used, ranging from 50 to $13 \times 10^6$ Da.

It should be noted that "average molecular weight" here means the weight-average molecular weight, calculated by the "intrinsic viscosity" method (Terbojevich et al., Carbohydr Res, 1986, 363-377).

One of the fundamental characteristics of HA is that it can be variously modified from the chemical standpoint, to transform its rheological and mechanical characteristics while maintaining its biological characteristics unchanged.

The Applicant has surprisingly found that of the numerous HA derivatives known to the prior art (esters, N- and O-sulphated derivatives, inner esters, etc.), the most suitable for the application described here are those obtained by formation of an amide bond between the carboxyl of the glucuronic acid residue and the hexadecylamine. The Applicant has also demonstrated that these derivatives not only cause a considerable reduction in pain symptoms, evaluated by comparison with the ozone treatment conventionally used in black disc disease, but also produce a wholly unforeseeable functional improvement.

DETAILED DESCRIPTION OF THE INVENTION

The present invention relates to pharmaceutical compositions in the form of hydrogels for use in the treatment of intervertebral disc degeneration, in particular the forms of dehydration and emptying of the nucleus pulposus known as "black disc disease". In particular the pharmaceutical compositions according to the present invention are effective in the treatment of pain in black disc disease and in the treatment required to correct the pelvic incidence angle and postural alterations associated with black disc disease.

Said compositions comprise a hyaluronic acid derivative which forms hydrogels with precise rheological characteristics that make it ideal for filling the nucleus pulposus. Specifically, the HA derivative used is hexadecylamide.

As previously stated, HA can have a MW ranging from 50 to $13 \times 10^6$ Da. The HA used in the present invention can derive from any source, such as extraction from rooster combs (EP138572), fermentation (from *Streptococcus equi* or *zooepidemicus*, EP716688), or biosynthesis (from Bacillus, WO2012032153, WO 2012032154), and have a weight average molecular weight ranging between 400 and $3 \times 10^6$ Da, in particular between $10^5$ Da and $10^6$ Da, and even more particularly between 500,000 and 730,000 Da.

The amide derivative used in the present invention is prepared from the latter fraction.

Hyaluronic acid amides are known to the skilled person; for example, the preparation of a wide range of hyaluronic acid amides (benzyl, octyl, dodecyl, etc.) is disclosed in EP1095064.

Only hexadecylamide prepared as described below is used according to the present invention. Briefly, hyaluronic acid pre-derivatised to a tetrabutylammonium salt (TBA) is solubilised in dimethylsulphoxide (DMSO), and methanesulphonic acid is added to the resulting solution. Carbonyldiimidazole is then added, and the mixture is left to react under stirring for one hour at room temperature. Hexadecylamine is then added, and the mixture is left to react for about 16-24 hours at 40°-42° C. A saturated solution of NaCl is then added to stop the reaction, and absolute ethanol is added to isolate the derivative by precipitation. The precipitate is washed first with a mixture of water and ethanol and then with ethanol alone, and finally dried under high vacuum.

The degree of derivatisation is modulated by varying the quantity of the reagents used and adapting the reaction times; the degree of derivatisation can be measured by methods known to the prior art, such as HPLC. In the ambit of the present invention, the degree of amidation used ranges from 0.1% to 10% molar, preferably from 1% to 3% molar, measured by HPLC after hydrolysis of the amide and conjugation of the hexadecylamine released with a fluorophoric substance.

Starting with the derivative thus obtained, a hydrogel can be formulated at a concentration ranging from 0.1 to 30 mg/ml, preferably 3 to 20 mg/ml, and even more preferably 5 to 15 mg/ml. The carriers preferably used are saline solution or phosphate buffer.

In the preferred pharmaceutical composition according to the present invention, the hyaluronic acid has an average MW ranging between 500,000 and 730,000 Da, the degree of molar amidation ranges between 1% and 3%, and the hyaluronic acid hexadecylamide concentration ranges between 5 and 15 mg/ml.

The hydrogel obtained undergoes a sterilisation process according to known techniques, for example in an autoclave, after being introduced into prefilled disposable syringes.

Regardless of the concentrations, the hydrogel obtained is easily extrudable, viscous to ensure that it remains in situ after application, elastic to ensure that it absorbs and redistribute loads, and highly hydratable; it also retains the biological characteristics of the starting polymer, hyaluronic acid, and is therefore biocompatible, bioresorbable and totally harmless to the body, both in its unmodified state and after enzymatic degradation.

In view of its particular characteristics, hydrogel can be associated with biologically or pharmacologically active substances (such as steroidal and non-steroidal anti-inflammatory drugs, cytokine inhibitors and local anaesthetics) deemed able to improve the symptoms of black disc. These substances can be inserted in the syringe on an extempore basis before application to the patient, so that the hydrogel functions both as a treatment for black disc and as a carrier of active substances.

Some preparation examples are set out below, for descriptive purposes only.

Example 1

Preparation of Hexadecylamide Derivative of HA with a Weight Average Molecular Weight Ranging Between 500 and 730 kDa and a Molar Amidation Content Ranging Between 1 and 3%

2 g of HA pre-derivatised to a TBA salt is solubilised in 200 ml of DMSO, and 64 µA of methanesulphonic acid is added to the resulting solution; 52 mg of 1-1'-carbonyldiimidazole is then added and left to react under gentle stirring for one hour at room temperature. 544 mg of hexadecylamine is then added, and the amidation reaction is conducted for 16-24 hours at 42° C. A saturated solution of NaCl is then added to stop the reaction, and 1.5 volumes of absolute ethanol are added after 15-30 minutes to isolate the derivative by precipitation. The precipitate is washed several times in 80:20 ethanol/water and then in ethanol alone, and finally dried under high vacuum at 40° C.

1.2 g of hexadecylamide derivative is obtained, whose degree of amidation, measured by HPLC, is about 2-3% molar.

Example 2

Preparation of a Hydrogel of the HA Hexadecylamide Derivative at the Concentration of 8 mg/ml, Obtained as Described in Example 1

2 g of HA hexadecylamide derivative, obtained as described in Example 1, is placed in a suitable recipient, and 250 ml of phosphate buffer (PBS) at pH 6.9 is added. The buffer contains 8.5 mg/ml NaCl, 0.45 mg/ml $Na_2HPO_4 \times 12H_2O$, and 0.11 mg/ml $NaH_2PO_4 \times 2H_2O$.

The mixture is left under stirring for at least 2 hours at room temperature, and for about 1 hour at 60° C. After this time, the T is returned to 20-25° C., and the mixture is left under stirring for 2-4 hours. The resulting mixture, which contains 8 mg/ml of hyaluronic acid hexadecylamide, is divided between glass syringes, which then undergo a damp heat sterilisation cycle (10 minutes) at about 121° C.

Example 3

Treatment of Patients Suffering from Black Disc Disease with HA Hexadecylamide vs. Ozone: Pilot Study By means of an NMR scan used for other diagnostic purposes, 11 patients with black disc disease at lumbar level (L3) were identified and treated according to the following protocol.

Materials and methods:
anaesthetic solution (1% carbocaine);
ozone 27 γ;
HA hexadecylamide hydrogel prepared as described in Example 2 (8 mg/ml);
technique: guided radioscopic infiltration, after cutaneous anaesthesia by infiltration; the puncture site was identified by observing the lumbar region in the two orthogonal projections;

The patients were divided into two groups:
A) 6 patients treated with 0.5 cc of hydrogel;
B) 5 patients treated with 3 cc of ozone 27 γ (control).

After treatment the patients were made to rest for several hours, and discharged with a paracetamol-based painkilling treatment if necessary. All the patients underwent a disability evaluation (RMDQ—Roland Morris Disability Questionnaire) and a pain evaluation (VAS—Visual Analogue Scale) and, after 6 months, a sagittal NMR scan to evaluate any variations in the pelvic incidence angle.

Results:
RMDQ: all patients in both groups reported a reduction in disability in terms of mobility and an improved quality of life, of comparable extents;
VAS scale: once again, all patients reported a definite reduction in pain, and this result, while expected for the group treated with ozone, is certainly surprising for Group A, which was treated with the derivatised HA hydrogel;
X-ray evaluation: in the patients in Group A, normalisation of the disc was observed; it appeared paler, and therefore hydrated, on the NMR scan, and very similar to the untreated healthy discs. The patients in Group A also presented a definite improvement in the pelvic incidence angle.

However, none of these functional effects were observed in the patients in Group B, treated with ozone: not only was there no improvement (normalisation) in the appearance of the disc, which actually worsened in 3 cases, but the treatment had no effect on the pelvic incidence angle.

CONCLUSIONS

Although this is just one pilot study with a limited number of patients, it is evident that treatment with hyaluronic acid hexadecylamide has a surprisingly favourable effect not only on the symptoms, but above all on the functions, of patients suffering from black disc disease.

The data presented here unequivocally demonstrate that treatment with hyaluronic acid hexadecylamide not only has a painkilling effect comparable with that of ozone, but above all has an unexpected curative effect, which restores the hydration of the nucleus pulposus and corrects the postural defect manifested by all patients suffering from black disc disease.

The invention claimed is:

1. Method of treating "black disc disease", which comprises hydrating a nucleus pulposus by administering to a patient in need thereof an effective amount of a hydrogel of hyaluronic acid hexadecylamide;
    wherein the hyaluronic acid has an average molecular weight MW ranging between 500,000 and 730,000 Da and a degree of molar amidation ranging between 1% and 3%, and the concentration of the hyaluronic acid hexadecylamide is 8 mg/ml.

2. The method according to claim 1, wherein the hydrogel further comprises pharmaceutically or biologically active substances.

3. The method according to claim 2, wherein pharmaceutically or biologically active substances are chosen from steroidal and non-steroidal anti-inflammatory drugs, cytokine inhibitors and local anaesthetics.

4. The method according to claim 1, which comprises treating pain in black disc disease.

5. The method according to claim 1, correctively treating the pelvic angle of incidence and the postural alterations connected with black disc disease.

* * * * *